United States Patent [19]

Obermajer

[11] 4,326,539
[45] Apr. 27, 1982

[54] PROCESS FOR MEASURING THE CARDIAC VOLUME

[76] Inventor: Wladimir Obermajer, 1 villa Léandre, 75018 Paris, France

[21] Appl. No.: 134,290

[22] Filed: Mar. 27, 1980

Related U.S. Application Data

[63] Continuation-in-part of Ser. No. 964,166, Nov. 28, 1978, abandoned.

[51] Int. Cl.³ .............................................. A61D 5/02
[52] U.S. Cl. ................................... 128/713; 364/415; 73/204
[58] Field of Search .................. 128/700, 713; 73/204; 364/415–416

[56] References Cited

U.S. PATENT DOCUMENTS 4,035,622 7/1977 Obermajer ......................... 128/713
4,137,910 2/1979 Murphy .............................. 128/700

OTHER PUBLICATIONS

Ellis, R. J. et al., "Computerized Monitoring of Cardiac Output by Thermal Dilution," Jourl. Assn. Adv. Med. Instrum. v. 6#2, Mar.–Apr. 1972 pp. 116–121.

Primary Examiner—Robert W. Michell
Assistant Examiner—Francis Jaworski
Attorney, Agent, or Firm—Holman & Stern

[57] ABSTRACT

The invention relates to a process for the measurement of cardiac volumes of the beating heart, in pulsed flow conditions, by means of a tracer injected upstream of or in the ventricle at a controlled injection flow $D_i$ during a controlled injection time $t_i$. The variation of concentration $\Delta$ of the tracer with respect to time, in a pulsed flow regime varies in a steplike manner, the concentration at each cardiac cycle n being $\Delta n$.

According to the invention, after acquiring the concentration $\Delta$ of the tracer during a number N of complete cardiac periods and computing the step concentration $\Delta n$, the mean cardiac period $\bar{\tau}$ from the number of recorded cardiac cycling intervals n, the following summated concentration products can be formed:

$$S = \bar{\tau}(1;N) \cdot \sum_{n=1}^{N} \Delta_n \qquad S' = \bar{\tau}(m;N) \cdot \sum_{n=m}^{N} \Delta_n$$

where m is any cycle corresponding to or occurring after the $M^{th}$ cardiac cycle but before the $N^{th}$ cycle ($M \leq m < N$), where M is the cycle at which at maximum step concentration of tracer occurs, where N is a conveniently great number of cycles encompassing the measurement process and where 1 is the cardiac cycle corresponding to the first step of the tracer curve, where $\bar{\tau}(1;N)$ is the mean cardiac period over N cardiac cycles, and $\bar{\tau}(m;N)$ is the mean cardiac period over the (N-(m-1)) cardiac cycles, whence the cardiac volumes are determined from the measured values ($\Delta_n$, $\tau_n$) and from the aforementioned relationships (S, S').

7 Claims, 6 Drawing Figures

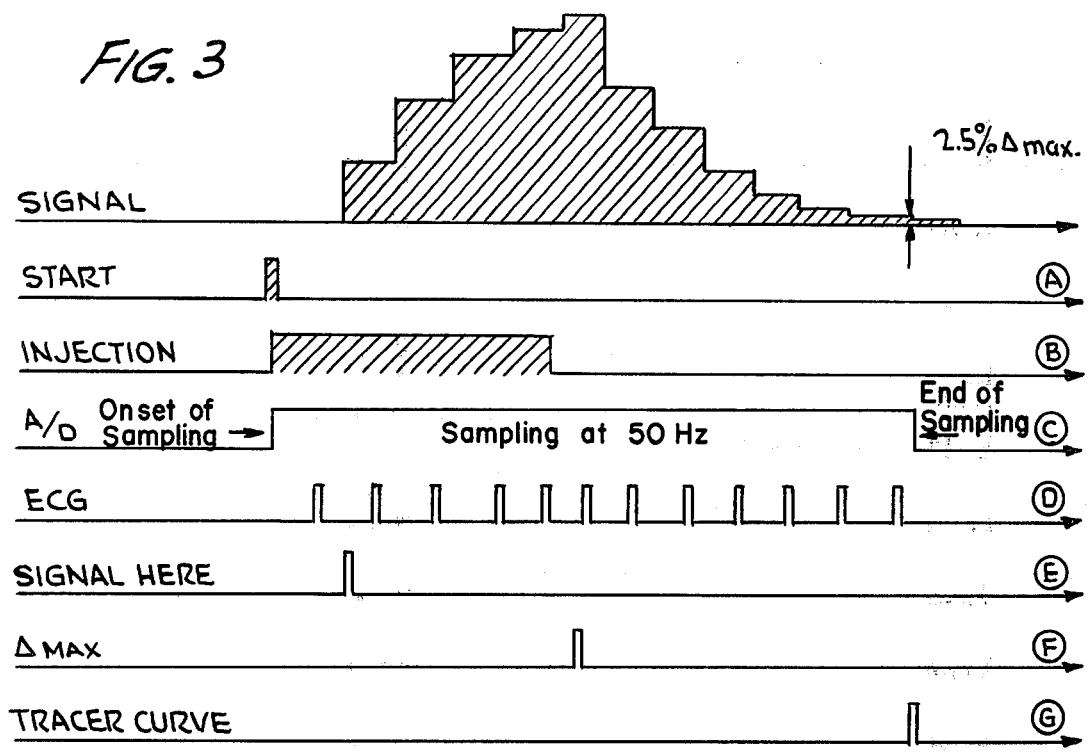
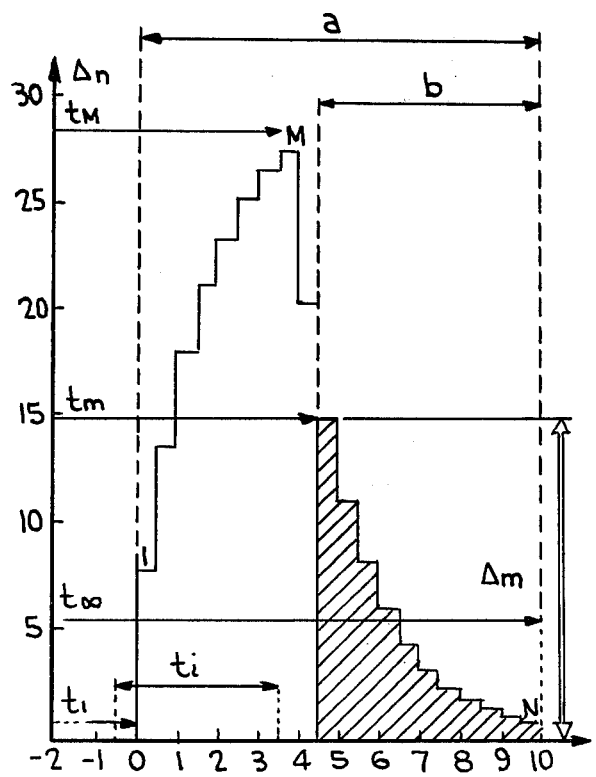
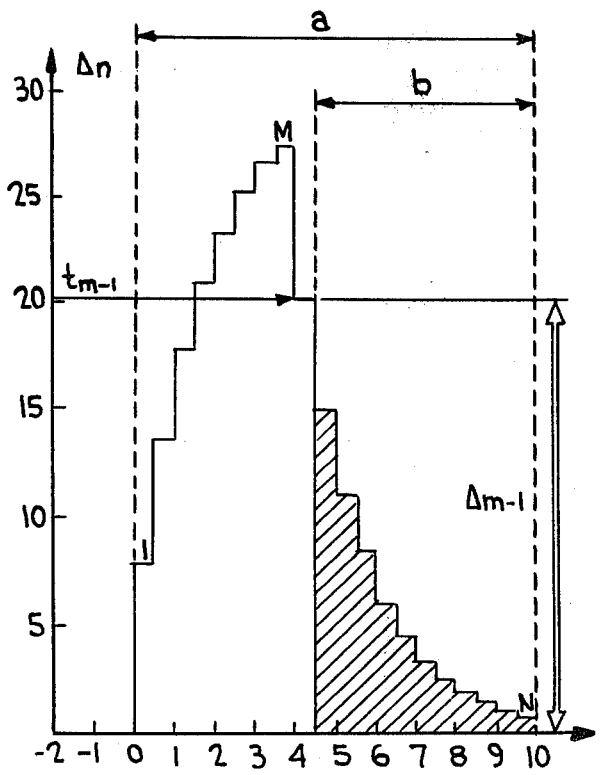

PROCESS FOR MEASURING THE CARDIAC VOLUME

CROSS REFERENCE TO PARENT APPLICATION

This application is a continuation-in-part application of U.S. patent application No. 964,166, filed Nov. 28, 1978, and now abandoned.

BACKGROUND OF THE INVENTION

The present invention relates to a process and apparatus for measuring the cardiac capacity.

A process and an apparatus of this type have been described in U.S. Pat. No. 4,035,622.

According to the process which is the subject of the U.S. Pat. No. 4,035,622 "a quantity $Q_i$ of tracer (e.g. dye or cold liquid) is injected at constant injection flow rate $D_i$ during a time $t_i$ corresponding to at least two heart beats (two cardiac cycles), the concentration $\Delta_m$ of tracer in the blood (or the change in blood temperature) is measured at the time $t_m$ of the end of the tracer injection and, $\Delta(t)$ being the tracer concentration (or the change of temperature) as a function of time t taking $t=0$ at the onset of injection, one measures the integrals.

$$S = \int_0^\infty \Delta(t)\, dt \text{ and } S' = \int_{t_m}^\infty \Delta(t)\, dt,$$

thus the cardiac capacity V is computed using the subsequently measured values".

But it has been established that cardiac volumes and more precise results concerning flow measurement can be obtained if some modifications are brought to the procedure by taking into account the pulsatile or non steady flow conditions of the beating heart. The modifications take into account a heart-beat by heart-beat analysis of the concentration variation and of the cardiac period $\tau_n$; that because the beating heart includes the cardiac valve system, the concentration variation changes in a discontinuous stepwise manner; that the period $\tau_n$ of a cardiac cycle can change over the time needed for the measurement to take place; that the washout part of the tracer curved is delayed with respect to the end of injection and takes place not at the end of injection but a little later and that subsequently not only the concentration variation has to be sampled at a given rate (e.g. 50 samples/sec) but also that the concentration level has be determined and stored at each cardiac cycle as well as the period $\tau_n$ of each of these cardiac cycles.

SUMMARY OF THE INVENTION

In the process of the present invention, one injects according to the known process, a quantity $Q_i$ of tracer at constant flow rate $D_i$ during a time $t_i$, but with the difference to the known process that, in the first place one records the stepwise concentration $\Delta_n$ of the tracer during a number N of complete cardiac periods n, and in the second place one determines the cardiac cycle M at which the maximum of the tracer concentration $\Delta_M$ occurs; subsequently the parameters, the cardiac periods $\tau_n$, the fraction $\phi_n$ of the $n^{th}$ cardiac cycle during which tracer injection takes place (assuming that injection can start or stop on the middle of one cycle) and the mean cardiac period $\tau$, are measured or determined as a first step for calculating the following summation products.

$$S = \tau(1;N) \cdot \sum_{n=1}^{N} \Delta_n$$

$$S' = \tau(m;N) \cdot \sum_{n=m}^{N} \Delta_n$$

Where m is any cardiac cycle corresponding to or occuring after the $M^{th}$ cycle but before the $N^{th}$ cycle ($M \leq m < N$) where M is the cycle at which the maximum step concentration of tracer occurs, where N is a conveniently great number of cycles encompassing the measurement process and where 1 is the first cardiac cycle corresponding to the first step of the tracer curve, where $\tau(1;N)$ is the mean cardiac period over N cardiac cycles $$\left( \bar\tau(1;N) = \frac{1}{N} \cdot \sum_{n=1}^{N} \tau_n \right)$$

and $\tau(m;N)$ is the mean cardiac period over the $(N-(m-1))$ cardiac cycles $$\left( \tau(m;N) = \left( \frac{1}{N - (m-1)} \right) \cdot \sum_{n=m}^{N} \tau_n \right)$$

and in a second computational step the cardiac volumes are determined from the recorded values and the values determined in the first step.

In practice, the concentration $\Delta$ has to be sampled and stored at a given rate (e.g. 50 cycles/sec) over N cardiac cycles. It is understood that $\Delta$ is the sample concentration value as opposed to $\Delta_n$ which is the step concentration value at the $n^{th}$ cardiac cycle. Concurrently, the length of the cardiac periods $\tau_n$ are measured and recorded.

The recorded tracer curve is then analysed so as to determine the value of the concentration at each cardiac cycle ($\Delta_n$) and the recorded $\tau_n$ are summated to determine the mean cardiac cycle over 1 to N and m to N.

The sum $$S = \tau \cdot \sum_{n=1}^{N} \Delta_n$$

would be equal to the integral or the area under the tracer curve only if the cardiac cycles $\tau_n$ are equal.

Otherwise one always has the relationship $$\int_0^{t_N} \Delta(t) \cdot dt = \sum_{q=1}^{Q} (\Delta_q \cdot \tau_q') \neq \tau \cdot \sum_{n=1}^{N} \Delta_n$$

where $\tau_q'$ would of course be the sampling period (in case of a practical application) and not the heart period $\tau_n$; $t_N$ and Q are respectively the integration and summation limits equivalent to the chosen $N^{th}$ step.

The result of these considerations is that instead of using time integrals as previous authors, one uses a summation method to obtain the calculation parameters for determining end-systolic, end-diastolic and stroke cardiac volumes.

Furthermore, even if in theory m can be any cycle corresponding to or occuring after the $M^{th}$ cycle, in practice for reasons of precision the step m is taken at the $M^{th}$ cardiac cycle if tracer injection has ended in the previous cycle, otherwise m is taken at the $(M+1)^{th}$ cycle.

One can show that the pre-systolic or end-diastolic cardiac volume $V_T$ can be computed from:

$$V_T = \frac{D}{\Delta_m} \cdot S' \quad M \leq m < N$$

and the residual or end-systolic volume $V_R$ by the equation:

$$V_R = \frac{D}{\Delta_{m-1}} \cdot S' \quad M+1 \leq m < N$$

D being the cardiac output determined by a classical method or by computing D from $D = Q_i/S$, $\Delta_m$ and $\Delta_{m-1}$ being the tracer concentrations at the $m^{th}$ and $(m-1)^{th}$ cardiac cycle.

The volumes $V_T$ and $V_R$ can also be computed from:

$$V_T = \frac{Q_i}{m} \cdot \frac{S'}{S} \quad M \leq m < N$$

and $$V_R = \frac{Q_i}{\Delta_{m-1}} \cdot \frac{S'}{S} \quad M+1 \leq m < N$$

$$V_T = \frac{(\phi_n \cdot v) - \frac{(Q_i \cdot \Delta_{n-1} \cdot \bar{\tau})}{S}}{(\Delta_n - \Delta_{n-1})} \quad 1 \leq n < M$$

$$V_R = \frac{(\phi_n \cdot v) - \frac{(Q_i \cdot \Delta_n \cdot \bar{\tau})}{S}}{(\Delta_n - \Delta_{n-1})} \quad 1 \leq n < M$$

where v is the injectate-volume-per-heartbeat quantity ($v = D_i \cdot \tau_n$), where $\phi_n$ is the fraction of the $n^{th}$ cardiac cycle during which injection takes place ($0 < \phi_n \leq 1$) and where $\Delta_n$ and $\Delta_{n-1}$ are chosen such that $$\frac{\Delta_n - \Delta_{n-1}}{\Delta_n} > 5\%, \Delta_{n-1} \geq 0 \text{ and } \Delta_n > 0.$$

If no values satisfy the aforementioned conditions, than $V_T$ and $V_R$ cannot be computed during the tracer concentration increase phase on the tracer curve.

For the washout part of the tracer curve the following relations hold:

$$V_T = \frac{Q_i \cdot \Delta_m \cdot \bar{\tau}}{(\Delta_m - \Delta_{m+1}) \cdot S} \quad M \leq m < N$$

and $$V_R = \frac{Q_i \cdot \Delta_{m+1} \cdot \bar{\tau}}{(\Delta_m - \Delta_{m+1}) \cdot S} \quad M \leq m < N$$

To obtain the best practical precision m has to be taken as close as possible to M i.e. $\Delta_m$ is taken to be $\Delta_M$ or $\Delta_{M+1}$ and $\Delta_{m+1}$ is taken to be $\Delta_{M+1}$ or $\Delta_{M+2}$ respectively.

In a preferred embodiment of the process, an apparatus according to the invention will be used which consists of a tracer injection system, or injector, giving controllable flow, a transducer able to measure the variation of tracer concentration downstream of the point of injection, and the necessary recording devices to store the value of the tracer concentration $\Delta_n$ at each cardiac cycle n as well as the means to sum these values; in the first case, the summation product is performed over the N cardiac cycles of the measurement procedure and in the second case the summation product is performed between the $m^{th}$ and the $N^{th}$ cardiac cycles; the means of determining the appearance of the first cardiac cycle which corresponds to the onset of the tracer curve, the cycle M at which maximum step concentration $\Delta_M$ occurs and the $N^{th}$ cycle at which concentration has fallen below a preset value; the means of determining the concentration $\Delta_n$ and the cycle number n for at least two consecutive heart beats following the $M^{th}$ cardiac cycle; the facilities permitting the recording of the duration of each cardiac period $\tau_n$ and the means of determining the average value of the period $\bar{\tau}$, firstly over the N cardiac cycles of the measurement and secondly between the $m^{th}$ and the $N^{th}$ cardiac cycle.

In practice, a converter is associated with a tracer sensing transducer to transform the output of the transducer to an electrical signal which is applied to an amplifier and converted into numerical values by an analog digital (A/D) converter.

A sequence generator controls the onset of the measurement procedure, the initialisation of the tracer injection, the A/D converter, the memory banks, the data analyser, the calculator and the display. The memory banks are dedicated firstly to the storage of the concentration sample values $\Delta$, the period length $\tau_n$, the data relevant to the cycle indexation and secondly after the data have been analysed, for the storage of the step concentration values $\Delta_n$ and $\Delta_m$ for the product summations S and S' and for the average period.

It will be understood that depending on the characteristics of the transducer the technology exists for converting the output signal from the transducer into meaningful association with tracer concentration.

BRIEF DESCRIPTION OF THE DRAWINGS

The following description with reference to the drawing gives an example of the incorporation of the invention into a system and more particularly according to a preferred embodiment. This system permits the simultaneous display of the cardiac output (D) and the cardiac end-diastolic ($V_T$) and the residual volumes ($V_R$).

FIG. 3 shows the different time sequences of the sequence generator of FIG. 1.

FIGS. 5 and 6 show the theoretical stepwise variation in arbitrary units of a tracer dilution curve as a function of time in a heart, beating 120 times per minute.

FIG. 5 illustrates the nomenclature and parameters for the determination of the pre-systolic (or end-diastolic) volume $V_T$. Similarly FIG. 6 shows the elements for calculation of the end-systolic (or residual) volume $V_R$.

DETAILED DESCRIPTION OF THE PREFERRED EMBODIMENT

The system consists of a transducer (1) which is placed, by means of a conventional catheterisation technique, downstream of the right or left ventricle as close as possible to the outlet valve, the pulmonary or aortic valve, depending upon which ventricle is to be investigated. The transducer (1) is connected to an interface (2) which converts the concentration dependent output of the transducer into an analogic-electrical signal, the said electrical signal is then amplified and converted into numerical values by means of an A/D converter. In the case for thermodilution the transducer is a thermistor and the interface consists of a measuring bridge, an amplifier and an A/D converter.

Figure 1:
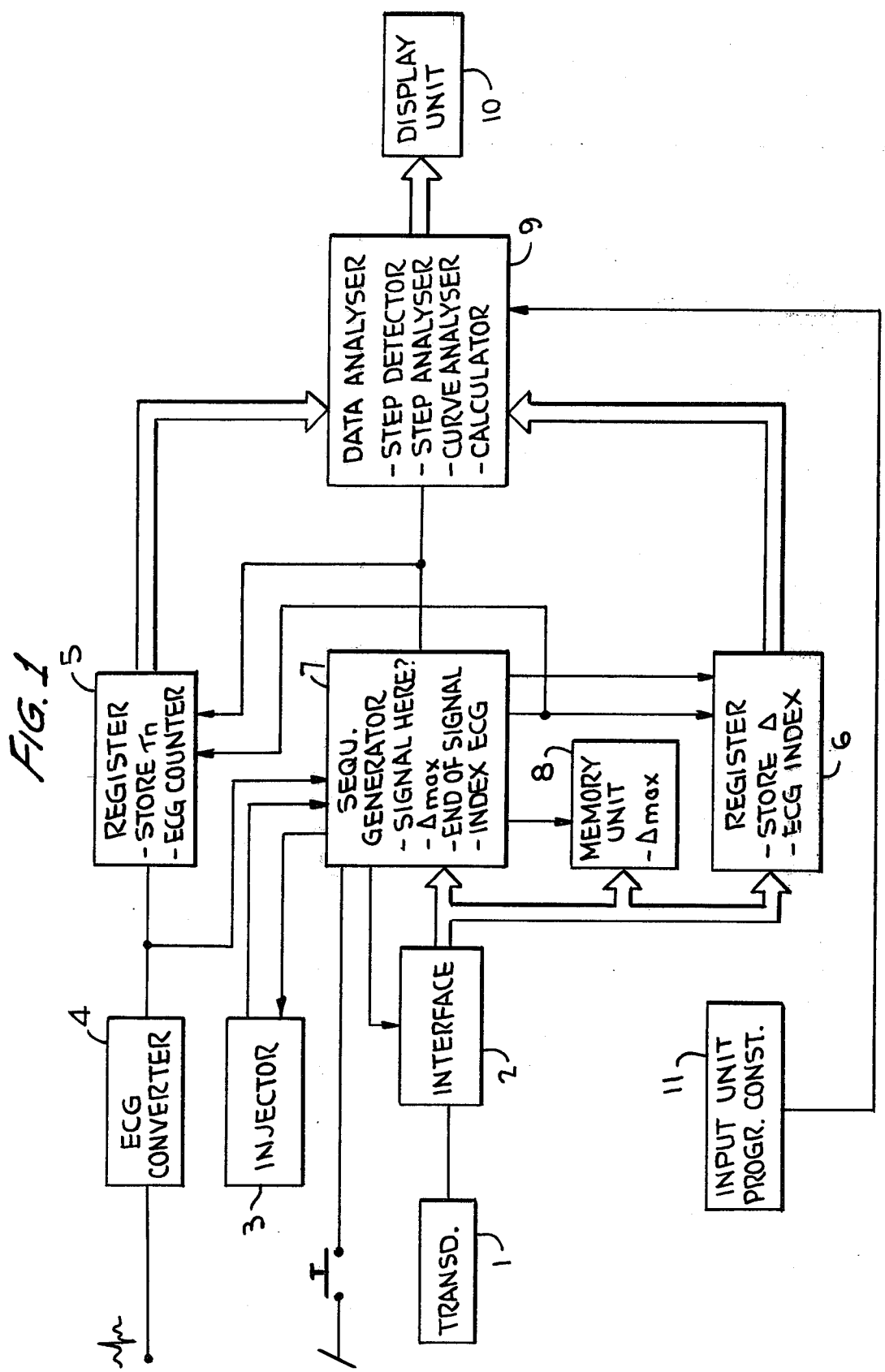
FIG. 1 represents the synoptic of the different functions of the system constituting the preferred embodiment.
Figure 2:
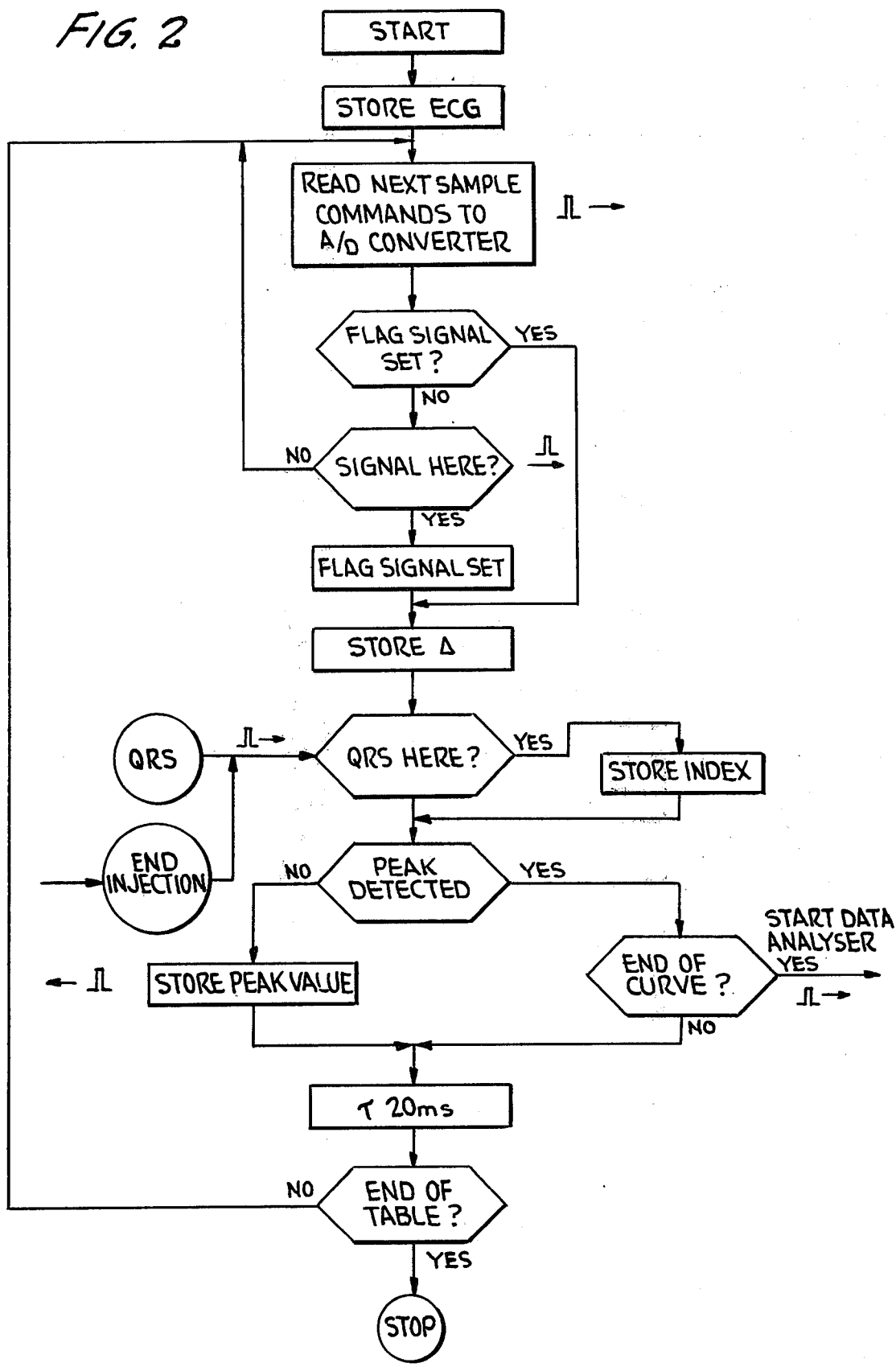
FIG. 2 is a flow chart showing how the sequence generator (7) of FIG. 1 operates.

A sequence generator (7) controls the different operations and, more particularly (as can be seen in the flow chart of FIG. 2), the onset and the end of tracer injection, the volume of injected tracer, the sampling and the storage of the interface output signal $\Delta$, the storage of the maximum concentration variation $\Delta_{max}$, the storage and the indexation of the cardiac periods $\tau_n$ and the initialisation of the analysis of the recorded data. The cardiac cycle during which tracer injection stops is memorized in the register of the data analyser (9).

Once the manual switch (12) is activated, the sequence generator (7) starts the injection and initiates the data sampling; as soon as the injection starts, the cardiac periods $\tau_n$ are stored in register (5) and the sampled concentration values $\Delta$ are stored in the memories of register (6). It is understood that $\Delta$ is the sample concentration value as opposed to $\Delta_n$ which is the step concentration value at the $n^{th}$ cardiac cycle. The electrocardiogram (ECG) signal enters and ECG converter (4) which generates a logic signal whose pulse corresponds to the qrs complex and whose pulse width is 30 ms. (In order that at least one concentration sample $\Delta$ is taken during the appearance of the QRS pulse width of the ECG, the concentration sampling rate has been set to 50 cycles/sec.) in the preferred embodiment if two sample values $\Delta$ occur during the QRS complex pulse width, the first concentration sample value is taken into consideration. At each cardiac cycle i.e. at each QRS complex, the sequence generator indexes the said cardiac cycle and stores the index n and the corresponding value of the concentration $\Delta$ into the register (6). The first QRS complex corresponding to the beginning of the first cardiac cycle of the measurement procedure is the QRS complex occurring just before the onset detection of the tracer curve. The sequence generator (7) also detects the maximum value of the concentration $\Delta_{max}$ and stores the said value into memory unit (8). $\Delta_{max}$ is the maximum concentration value of the sample values $\Delta$ sampled at the rate of 50 cycles per second. This value is not necessarily equal to the maximum step concentration value $\Delta_M$. As soon as the value of the concentration drops below a preset fraction of the maximum concentration $\Delta_{max}$ stored in (8), the sequence generator (7) stops the data acquisition and starts the data analyser (9).

Figure 4:
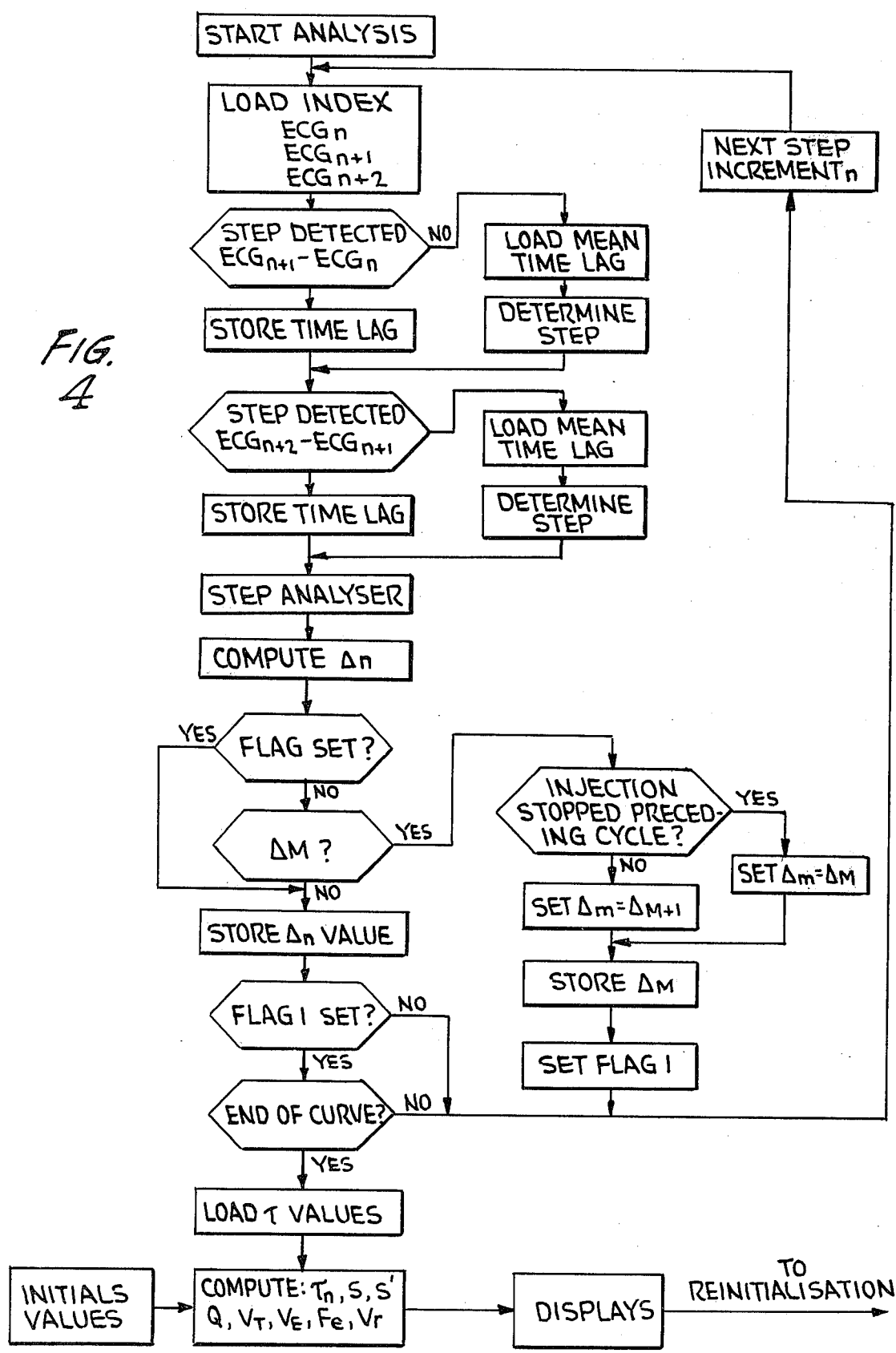
FIG. 4 shows how the data analyser (9) of FIG. 1 determines the different steps n and how it calculates the step concentration values $\Delta_n$ from the sampled concentration values $\Delta$. (The computed volume are the end-diastolic volume $V_T$, the residual volume $V_R$ and the ejected volume $V_E = V_T - V_R$. The ejected volume and the total volume are used to compute the ejection fraction $Fe = V_E/V_T$.

The data analyser (9), which incorporates a register, a step detector, a step analyser, a curve analyser and a calculator, determines the step concentration value $\Delta_n$ at each step, performs the necessary summation products (S,S') of the said concentration values and computes the cardiac volumes ($V_T$ and $V_R$) and the cardiac flow D. (The flow chart of the data analyser functions is shown in FIG. 4). The indexed cardiac cycles and the corresponding concentration values $\Delta$ are read from the register (6) by the data analyser (9). The concentration values $\Delta$ between two consecutive indices are analysed by the step detector whose function is to detect the onset of each concentration step occuring between two consecutive QRS complexes. In the preferred embodiment, the step detector determines the slope variation between five consecutive samples as well as the absolute concentration value variation over these five steps. Once the step onset is detected, the step detector analyses ten samples of concentration $\Delta$ before and after the said step onset to make sure that the step detector did not take an artefact into consideration. The concentration value $\Delta$ and its address in register (6), corresponding to the start of the step, are then memorized. The time lag between the QRS complex appearance and the start of the step on the tracer curve is also memorised. The said time lag is used to associate each concentration step $\Delta_n$ to its corresponding cardiac cycle n. The mean time lag is also used to predict step onset in case the step detector is unable to determine the onset of the concentration step within two consecutive QRS complexes (eg. the case of a large residual volume and small cardiac volume certain portions of the tracer curve have indefinite steps onsets). In the most extreme condition the mean time lag would simply be the time lag between the first QRS complex and the onset of the tracer curve.

The different steps of the tracer curve being now defined, the step analyser analyses the concentration sample values $\Delta$ within two consecutive step onsets, determined by the step detector in order to determine the step concentration value $\Delta_n$. In the preferred embodiment the step analyser determines the concentration $\Delta_n$ of each step by considering the five concentration values before the step onset and by using a smoothing algorithm, generates a representative or "best" value for $\Delta_n$.

The curve analyser compares the step concentration values $\Delta_n$ computed by the step analyser and determines the cardiac cycle M at which the maximum concentration $\Delta_M$ occurs. The said curve analyser takes the step concentration value $\Delta_m$ at the $M^{th}$ cardiac cycle if the tracer injection stopped in the preceding cycle and takes the step concentration value $\Delta_m$ at the $(M+1)^{th}$ cardiac cycle, if tracer injection was still taking place during the $M^{th}$ cardiac cycle at which maximum step concentration value $\Delta_M$ occured. The step concentration value $\Delta_m$ of the $M^{th}$ or $(M+1)^{th}$ cardiac cycle and the step concentration value $\Delta_{m+1}$ of the $(M+1)^{th}$ or $(M+2)^{th}$ cardiac cycle respectively are stored in the register of the data analyser (9).

The cardiac cycle periods $\tau_n$ stored in the register of (5) are used to compute the average cardiac period over the two intervals 1 to N and m to N, as explained above in the summary of the invention.

The calculator reads the memory content of the register contained in the data analyser (9). The stored values $\Delta_m$, $\Delta_{m+1}$, $\bar{\tau}$, $\Delta_n$ are used to compute the summation product S, S' and reading the preprogrammed constants introduced before each measurement into unit (11), the said calculator computes the cardiac volumes $V_T$, $V_R$ and the cardiac output D. The input constants are introduced into unit (11) by means of a dial-in system (with or without a reference transducer) which enables the data analyser (9) to scale and calibrate the aforementioned computed values. In the case of thermodilution constants defining the thermistance and the quantity of injectate are dialled-in and the injectate reference temperature is introduced either by dial-in or by means of a reference thermistor connected into unit (11) and indicating the tracer injectate temperature. The computed values are finally displayed on the display unit (10) and the sequence generator (7) resets the system so as to be ready for a new measurement procedure.

In the dilution curve of FIGS. 5 and 6, for a heart, beating 120 times per minute, where $t_i$ is the total time that tracer is present in the atrium and therefore is not related to the lagtime between atrial and ventricular injectate appearance on a per-beat basis.

What is claimed is:

1. A process for the measurement of cardiac volumes of the beating heart, in pulsed flow conditions by dilution of a quantity $Q_i$ of tracer injected upstream of a ventricle, at controlled injection flow $D_i$ and during a controlled time $t_i$ comprising the steps of: recording the stepwise tracer concentration $\Delta_n$ during a number N of complete cardiac periods n, by means of a transducer downstream of the injection site; and determining the cycle M at which maximum step concentration value $\Delta_M$ occurs, as well as the mean cardiac cycling intervals, i.e. the cardiac period $\tau_n$, whereby forming the following summation products:

$$S = \bar{\tau}(1;N) \cdot \sum_{n=1}^{N} \Delta_n$$

$$S' = \bar{\tau}(m;N) \cdot \sum_{n=1}^{N} \Delta_n$$

where m is any cycle corresponding to or occurring after the $M^{th}$ cardiac cycle but before the $N^{th}$ cycle ($M \leq m < N$), where M is the cycle at which the maximum step concentration value $\Delta_M$ of tracer occurs, where N is a conveniently great number of cycles encompassing the measurement process and where 1 is the cardiac cycle corresponding to the first step of the tracer curve, where $\tau(1;N)$ is the mean cardiac period over N cardiac cycles $$\left( \bar{\tau}(1;N) = \frac{1}{N} \cdot \sum_{n=1}^{N} \tau_n \right)$$

and $\bar{\tau}(m;N)$ is the mean cardiac period over the $(N-(m-1))$ cardiac cycles $$\left( \bar{\tau}(m;N) = \left( \frac{1}{N-(m-1)} \cdot \sum_{n=m}^{N} \tau_n \right) \right)$$

thereby determining the cardiac volumes are determined from the measured values $(\Delta_n, \tau_n)$ and from the aforementioned relationships (S,S').

2. A process according to claim 1, further comprising the step of computing the end-diastolic or pre-systolic cardiac volume $V_T$ and end-systolic or residual volume $V_R$ from the equation:

$$V_T = \frac{D}{\Delta_m} \cdot S \quad M \leq m < N$$

and $$V_R = \frac{D}{\Delta_{m-1}} \cdot S' \quad M+1 \leq m < N$$

where D is the cardiac output determined by a classical method, $\Delta_m$ and $\Delta_{m-1}$ being the tracer step concentration values at the $m^{th}$ and $(m-1)^{th}$ cardiac cycles.

3. The process according to claim 1, further comprising the step of computing the end-diastolic or pre-systolic cardiac volume $V_T$ and the end-systolic or residual volume $V_R$ from the equations:

$$V_T = \frac{Q_i}{\Delta_m} \cdot \frac{S}{S'} \quad M \leq m < N$$

$$V_R = \frac{Q_i}{\Delta_{m-1}} \cdot \frac{S}{S'} \quad M+1 \leq m < N.$$

4. A process according to claim 1, further comprising the step of computing the end-diastolic or pre-systolic cardiac volume $V_T$ and the end-systolic or residual volume $V_R$, using any pair of cardiac cycles n and n−1 occurring between the first cardiac cycle of the onset of the dilution curve (1) and the $M^{th}$ cardiac cycle at which the maximum step concentration $\Delta_M$ occurs, from the equations:

$$V_T = \frac{(\phi_n \cdot v) - \frac{(Q_i \cdot \Delta_{n-1} \cdot \bar{\tau})}{S}}{(\Delta_n - \Delta_{n-1})} \quad 1 \leq n < M$$

and $$V_R = \frac{(\phi_n \cdot v) - \frac{(Q_i \cdot \Delta_n \cdot \bar{\tau})}{S}}{(\Delta_n - \Delta_{n-1})} \quad 1 \leq n < M$$

where $\Delta_n$ is the step concentration value at the $n^{th}$ cardiac cycle, where $\phi_n$ is the fraction of the $n^{th}$ cardiac cycle during which injection takes place ($0 < \phi_n < 1$), where $\Delta_n$ and $\Delta_{n-1}$ are chosen such that $$\frac{\Delta_n - \Delta_{n-1}}{\Delta_n} > 5\%,$$

$\Delta_{n-1} \geq 0$ and $\Delta_n > 0$, $\bar{\tau}$ being the mean cardiac cycle and where v is the injectate-volume-per-heartbeat quantity defined by the relationship: $v = D_i \tau_n$.

5. A process according to claim 1, further comprising the step of computing the end-diastolic and pre-systolic volume $V_T$ and the end-systolic or residul volume $V_R$ from the $m^{th}$ cardiac cycle included between the $M^{th}$ cardiac cycle needed to reach the maximum step concentration $\Delta_M$ and the $N^{th}$ cardiac cycle at which the value reached by the step concentration $\Delta_m$ is sufficiently small, from the equations:

$$V_T = \frac{\frac{(Q_i \cdot \Delta_m \cdot \bar{\tau})}{S}}{(\Delta_m - \Delta_{m+1})} \quad M \leq m < N$$

-continued $$V_R = \frac{\frac{(Q_i \cdot \Delta_{m+1} \cdot \bar{\tau})}{S}}{(\Delta_m - \Delta_{m-1})} \qquad M \leq m < N$$

where $\Delta_m$ is the step concentration value at the $m^{th}$ cardiac cycle and where $\bar{\tau}$ is the mean cardiac cycle.

6. Apparatus for measuring cardiac volume of the beating heart, in pulsed flow conditions by dilution of a quantity $Q_i$ of tracer injected upstream of a ventricle, at controlled injection flow $D_i$ and during a controlled time $t_i$ by recording the stepwise tracer concentration $\Delta_n$ during a number N of complete cardiac periods n downstream of the injection site, and by determining the cycle M at which maximum step concentration value $\Delta_M$ occurs, as well as the mean cardiac cycle period obtained by the recording of the cardiac cycling intervals, i.e. the cardiac period $\tau_n$, whereby forming the following summation products:

$$S = \bar{\tau}(1;N) \cdot \sum_{n=1}^{N} \Delta_n \qquad S' = \bar{\tau}(m;N) \cdot \sum_{n=m}^{N} \Delta_n$$

where m is any cycle corresponding to or occuring after the $M^{th}$ cardiac cycle but before the $N^{th}$ cycle ($M \leq m < N$), where M is the cycle at which the maximum step concentration value $\Delta_M$ of tracer occurs, where N is a conveniently great number of cycles encompassing the measurement process and where 1 is the cardiac cycle corresponding to the first step of the tracer curve, where $\tau(1;N)$ is the mean cardiac period over N cardiac cycles $$\left( \bar{\tau}(1;N) = \frac{1}{N} \cdot \sum_{n=1}^{N} \tau_n \right)$$

where $\bar{\tau}(m;N)$ is the mean cardiac period over the $(N-(m-1))$ cardiac cycles $$\left( \bar{\tau}(m;N) = \left( \frac{1}{N-(m-1)} \cdot \sum_{n=m}^{N} \tau_n \right) \right)$$

whence the cardiac volumes are determined from the measured values ($\Delta_n$, $\tau_n$) and from the aforementioned relationships (S,S'), said apparatus comprising:

an injector for controlling the injectate flow rate;
a transducer for measuring the variation in concentration downstream of the injection site;
means for sampling values of the tracer curve $\Delta$ at a fixed rate and for recording the sample values;
means for determining and for recording the step concentration value $\Delta_n$ of each cardiac cycle n;
means of recording the duration $\tau_n$ of each cardiac cycle;
means for determining the cardiac cycle M at which the step tracer concentration is maximum $\Delta_M$;
means for summing the tracer concentration $\Delta_n$ in the first case between the first and the last (N) cardiac cycles of the tracer curve and, in the second case, between a cardiac cycle corresponding to or occurring after the cardiac cycle M, at which the maximum step concentration $\Delta_M$ occurs, and the last cardiac cycle N of the dilution curve which is reached when the step concentration $\Delta_n$ drops below a preset fraction of the maximum step concentration $\Delta_M$;
means for determining the average value of the period $\tau_n$ of the cardiac cycle between the aforementioned same two time intervals;
and means for computing the cardiac volumes from the aforementioned determined and stored values.

7. Apparatus according to claim 6, further including:
a converter associated with said transducer for converting the output of the transducer into an electrical signal;
an amplifier;
means for applying said electrical signal to the input of said amplifier;
a sequence generator for controlling the injector;
an analog-digital converter;
a data analyzer including a step detector;
a step analyzer;
a curve analyzer;
a calcuator; and
means for controlling said analog-digital converter, said data analyzer, said step analyzer, said curve analyzer, and said calculator from said sequence generator.

* * * * *